US008679762B2

(12) United States Patent
Maki et al.

(10) Patent No.: US 8,679,762 B2
(45) Date of Patent: Mar. 25, 2014

(54) METHOD OF DETECTING HEPATITIS B VIRUS S ANTIGEN

(75) Inventors: Noboru Maki, Asaka (JP); Yasuyuki Fukuda, Wako (JP); Tatsuji Kimura, Fujimino (JP); Yoko Oda, Tokyo (JP); Chiharu Ohue, Wako (JP); Osamu Kusano, Wako (JP)

(73) Assignee: Advanced Life Science Institute, Inc. (JP)

( * ) Notice: Subject to any disclaimer, the term of this patent is extended or adjusted under 35 U.S.C. 154(b) by 916 days.

(21) Appl. No.: 11/663,517

(22) PCT Filed: Sep. 21, 2005

(86) PCT No.: PCT/JP2005/017420
§ 371 (c)(1),
(2), (4) Date: Jul. 25, 2007

(87) PCT Pub. No.: WO2006/033368
PCT Pub. Date: Mar. 30, 2006

(65) Prior Publication Data
US 2008/0193916 A1    Aug. 14, 2008

(30) Foreign Application Priority Data

Sep. 22, 2004  (JP) ................................. 2004-274852

(51) Int. Cl.
*C12Q 1/70*   (2006.01)
*C07H 21/04*  (2006.01)
*A61K 39/395* (2006.01)

(52) U.S. Cl.
USPC ...... 435/7.1; 424/130.1; 424/227.1; 435/7.92

(58) Field of Classification Search
None
See application file for complete search history.

(56) References Cited

U.S. PATENT DOCUMENTS 4,861,588 A * 8/1989 Neurath et al. ............... 530/324
5,693,497 A * 12/1997 Takamizawa et al. ....... 435/69.3

FOREIGN PATENT DOCUMENTS

| EP | 0919568 | 6/1999 |
| WO | 91/14703 | 10/1991 |
| WO | 94/21812 | 9/1994 |
| WO | 95/21189 | 8/1995 |
| WO | 99/66047 | 12/1999 |
| WO | 02/14871 | 2/2002 |

OTHER PUBLICATIONS

Ishikawa et al. (Journal of Immunology, 1998, vol. 161, p. 5842-5850).*
Ryu et al. (Hybridoma, 2002, vol. 19, p. 185-189).*
Netesova et al. (Journal of Medical 2003, vol. 71, p. 183-187).*
Lerner et al. PNAS 1981, vol. 78, p. 3403-3407.*
Liu et al.; "Naturally Occurring Hepatitis B Surface Gene Variants in Chronic Hepatitis B Virus Infection: Correlation with Viral Serotypes and Clinical Stages of Liver Disease;" Journal of Medical Virology; 2002; pp. 50-59; vol. 68.
Tai et al.; "Novel and Frequent Mutations of Hepatitis B Virus Coincide with a Major Histocompatibility Complex Class I-Restricted T-Cell Epitope of the Surface Antigen;" Journal of Virology, Jun. 1997; pp. 4852-4856; vol. 71, No. 6.
Hunt et al.; "Clinical Relevance of Hepatitis B Viral Mutations;" Hepatology; 2000; pp. 1037-1044; vol. 31, No. 5.
Chisari et al.; "Hepatitis B Virus Immunopathogenesis;" Annual Review of Immunology; 1995; pp. 29-60; vol. 13; Annual Review Inc.
Howard et al.; "Towards the Development of Synthetic Hepatitis B. Vaccines;" Viral Hepatitis and Liver Disease; 1988; pp. 1094-1101; Alan R. Liss Inc., New York.
Hiroaki Okamoto; "Nippon Rinsho, Bunshi Kan-En Uirusubyogaku, Kiso-Rinsho-Yobo;" Japanese Clinic, Molecular Hepatitis Virology, Fundamental-Clinic-Prophylaxis, Lower Volume, Hepatitis A, B, D, E Viruses; Oct. 26, 1995; pp. 212-222.
Thiers et al.; Transmission of Hepatitis B From Hepatitis-B-Seronegative Subjects; The Lancet; Dec. 3, 1998; pp. 1273-1276.
Keiji Mitamura; "Nippon Rinsho: Bunshi Kan-En Uirusubyogaku, Kiso-Rinsho-Yobo;" Japanese Clinic, Molecular Hepatitis Virology, Fundamental-Clinic-Prophylaxis, Lower Volume; Oct. 26, 1995; pp. 13-27.
Köhler et al.; Continuous Cultures of Fused Cells Secreting Antibody of Predefined Specificity; Nature; Aug. 1975; pp. 495-497; vol. 256.
Köhler et al.; Derivation of Specific Antibody-Producing Tissue Culture and Tumor Lines by Cell Fusion; Eur. J. Immunol.; 1976; pp. 511-519; vol. 6.
Hoogenboom, Hennie R.; Designing and Optimizing Library Selection Strategies for Generating High-Affinity Antibodies ; Trends in Biotechnology; Feb. 1997; pp. 62-70; vol. 15.
Mandel et al.; Calcium-dependent Bacteriophage DNA Infection; J. Mol. Biol.; 1970; pp. 159-162; vol. 53.
Carman, W. et al., "Vaccine-induced escape mutant of hepatitis B virus", 1990, Lancet, vol. 336, pp. 325-329.
Huang, Xinghua et al., "Hepatitis B virus (HBV) vaccine-induced escape mutants of HBV S gene among children from Qidong area, China", 2004, Virus Research, vol. 99, pp. 63-68.
Lerner, R. et al., "Chemically synthesized peptides predicted from the nucleotide sequence of the hepatitis B virus genome elicit antibodies reactive with the native envelope protein of Dane particles", 1981, Proc. Natl. Acad. Sci. USA, vol. 78, No. 6, pp. 3403-3407.
Zuckerman, J. et al., "Mutations of the surface protein of hepatitis B virus", 2003, Antiviral Research, vol. 60, pp. 75-78.

* cited by examiner

*Primary Examiner* — Agnieszka Boesen
(74) *Attorney, Agent, or Firm* — Thompson Coburn LLP (57) ABSTRACT

[PROBLEMS] To provide a probe useful in the detection of HBV or HBs antigen by which an escape mutant of hepatitis B virus (HBV) possibly occurring in a specimen can be detected; and a method of using the same.
[MEANS FOR SOLVING PROBLEMS] A probe capable of recognizing an epitope located on a peptide comprising the amino acid sequence of SEQ ID NO:1; and a method of detecting hepatitis B virus or hepatitis B virus s antigen by using this probe.

7 Claims, 1 Drawing Sheet

Secondary structure of HBs antigen (Model view)

SEQUENCE LISTING

<160> NUMBER OF SEQ ID NOS: 3

<210> SEQ ID NO 1
<211> LENGTH: 55
<212> TYPE: PRT
<213> ORGANISM: Hepatitis B virus

<400> SEQUENCE: 1

Leu Thr Ile Pro Gln Ser Leu Asp Ser Trp Trp Thr Ser Leu Asn Phe
1               5                   10                  15

Leu Gly Gly Ala Pro Thr Cys Pro Gly Gln Asn Ser Gln Ser Pro Thr
            20                  25                  30

Ser Asn His Ser Pro Thr Ser Cys Pro Pro Ile Cys Pro Gly Tyr Arg
        35                  40                  45

Trp Met Cys Leu Arg Arg Phe
    50                  55

<210> SEQ ID NO 2
<211> LENGTH: 27
<212> TYPE: DNA
<213> ORGANISM: Hepatitis B virus

<400> SEQUENCE: 2
gaattcctca caataccaca gagtcta                                        27

<210> SEQ ID NO 3
<211> LENGTH: 33
<212> TYPE: DNA
<213> ORGANISM: Hepatitis B virus

<400> SEQUENCE: 3
ggatccttaa aaacgccgca gacacatcca gcg                                 33

METHOD OF DETECTING HEPATITIS B VIRUS S ANTIGEN

CROSS-REFERENCE TO RELATED APPLICATIONS

This application is the national stage entry in the United States of International Application No. PCT/JP2005/17420 which was filed on Sep. 21, 2005 and claims priority to the Japanese Patent Application No. 2004-274852 which was filed on Sep. 22, 2004.

INCORPORATION OF SEQUENCE LISTING

A paper copy of the Sequence Listing and a computer readable form of the sequence listing on diskette, containing the file named "seq listing.3_20.txt" of 1054 bytes in size (measured in MS-DOS) was transmitted to the U.S. Patent Office on Mar. 21, 2007 and is herein incorporated by reference. This Sequence Listing consists of SEQ ID NOs: 1-3.

TECHNICAL FIELD

The present invention relates to a probe recognizing a novel epitope of hepatitis B virus (HBV) s antigen (HBs antigen) and a method of detecting HBV, or HBs antigen, by using the probe.

BACKGROUND ART

Diagnosis of viral infection is carried out mainly by a method of detecting a virus or a virus-related component (protein or nucleic acid) or by a method of detecting a specific antibody produced by the living body upon viral infection.

Usually, infection with HBV can be known by confirming the presence of HBs antigen or HBc antibody. As an indicator not only for infection with HBV but also for a clinical state of an HBV carrier or judgment of prognosis and treatment efficacy, the amount of hepatitis B virus e antigen (HBe antigen), an antibody to the antigen, or DNA of HBV (HBV-DNA) is measured.

Among antigens constituting HBV viral particles (HBV particles), HBs antigen is a major constitutional envelope protein on the surface of infectious HBV particle and is anchored in a hepatocyte-derived lipid bilayer in which a core particle containing HBV-DNA is enveloped. In blood from a patient infected with HBV, there are noninfectious small spherical particles or tubular particles consisting of HBs antigens. The small spherical particles are present most abundantly in blood, and about 1000 small spherical particles are observed per one or several HBV particles. A majority of HBs antigen test agents commercially available at present mainly detects HBs antigen in the form of small spherical particles.

Figure 1:
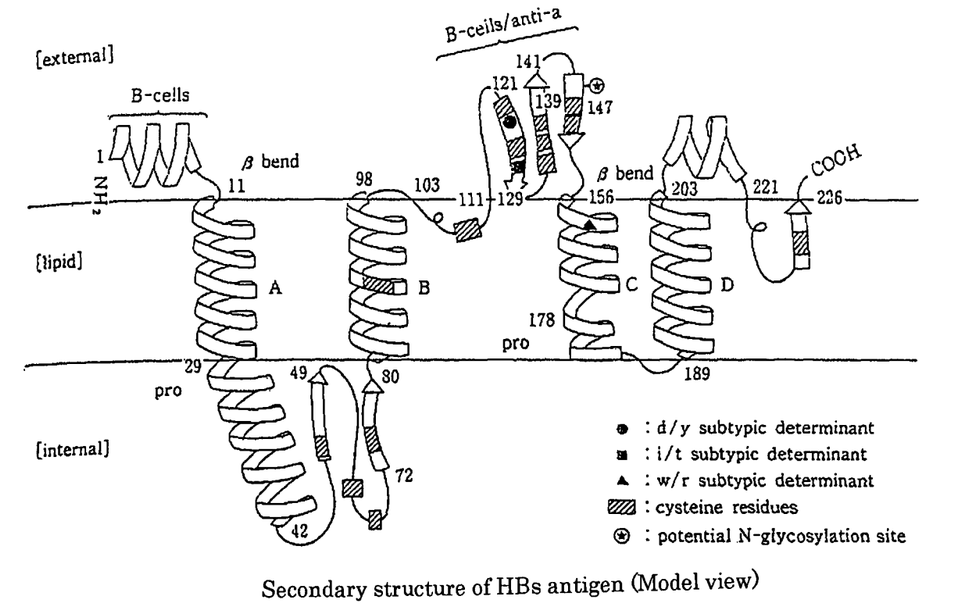
FIG. 1 shows an illustration of the secondary structure of HBs antigen.

HBs antigen is a membrane protein consisting of 226 amino acid residues (amino acid numbers 1 to 226) and penetrating 4 times through a lipid bilayer. Although a model of the transmembrane structure of HBs antigen is not fully elucidated, Howard et al. (Howard et al., Viral Hepatitis and Liver Disease (ed by Zuckerman A J, Alan R), pp. 1094-1101, Liss Inc., New York, 1988) have proposed that the HBs antigen is composed of a (ER lumen side) region, outside a lipid bilayer, consisting of positions 1 to 11 from the N-terminal of HBs antigen, a hydrophobic transmembrane region penetrating through a lipid bilayer consisting of positions 12 to 28, a region inside the lipid bilayer consisting of positions 29 to 80, a hydrophobic transmembrane region consisting of positions 81 to 97, a hydrophilic ER lumen region consisting of positions 98 to 156, and two hydrophobic transmembrane regions consisting of positions 157 to 226 (FIG. 1).

A main common "a" determinant used in detection of HBs antigen in conventional methods is positioned in the amino acid positions 110 to 156, contained in amino acids in the positions 98 to 156 localized at the ER lumen side, that is, on the surface of viral particle. This common "a" determinant is reported to consist of a complicated higher-order structure wherein at least 4 epitopes are present (Hiroaki Okamoto, "Nippon Rinsho, Bunshi Kan-En Uirusubyogaku, Kiso-Rinsho-Yobo" (Japanese Clinic, Molecular Hepatitis Virology, Fundamental-Clinic-Prophylaxis), Lower Volume, Hepatitis A, B, D, E Viruses, pp. 212-222, published on Oct. 26, 1995).

HBV is DNA virus, but HBV is known to undergo mutation comparable with RNA virus because during viral proliferation, its DNA is replicated into RNA, and from this RNA, DNA is synthesized by reverse transcriptase. Accordingly, it is estimated that mutants having various kinds of mutations occur in an individual infected with HBV. When external selective stress such as neutralizing antibody is applied to the HBV in such individual, there occurs the phenomenon in which HBV strains sensitive to the stress are decreased, while mutants resistant or insensitive to the stress are increased. The so-called "escape mutant" coming to be problematic in recent years is a mutant which has undergone substitution, deletion or insertion of amino acid(s) in the main common "a" determinant, thereby being endowed with an ability to maintain its infection by escaping from an antibody recognizing the "a" determinant before mutation.

One problem associated with occurrence of the escape mutant is that this mutant can keep persistent infection because it can escape from an antibody induced by inoculation with a vaccine utilizing the "a" determinant before mutation.

Another problem is that this escape mutant cannot be detected in conventional HBs antigen examination methods. Generally, the escape mutant having a mutation on the common "a" determinant has lower reactivity with a monoclonal antibody against the common "a" determinant in the wild-type HBV, and thus a monoclonal antibody against the wild-type common "a" determinant, used in conventional HBs antigen examination methods, cannot recognize the HBs antigen in the escape mutant type HBV, thus failing to find actually occurring HBV infection. For example, it is reported that a 145Arg mutant, that is, the mutant wherein amino acid at position 145 was changed from Gly in the wild type to Arg, has significantly lower reactivity with a monoclonal antibody against the common "a" determinant (Hiroaki Okamoto, "Nippon Rinsho, Bunshi Kan-En Uirusubyogaku, Kiso-Rinsho-Yobo" (Japanese Clinic, Molecular Hepatitis Virology, Fundamental-Clinic-Prophylaxis), Lower Volume, Hepatitis A, B, D, E Viruses, pp. 212-222, published on Oct. 26, 1995). Actually, it is reported that transfusion of blood, shown to be HBs antigen-negative in a screening test of HBV by using the conventional HBs antigen measurement reagent, caused infection with HBV (Thiers et al. Lancet, ii, 1273-1276, 1988).

In acute infection with HBV, there is a reported phenomenon in which an HBV-infected patient is HBs antigen-positive in an initial stage of infection and then turns HBs antigen-negative and simultaneously becomes HBs antibody-positive. The reason that the patient becomes HBs antibody-positive is that an antibody against the common "a" determinant of HBs antigen is produced in the body of the patient. The patient's antibody against the common "a" determinant binds to the same region as in the common "a" determinant recognized by a monoclonal antibody used in the HBs antigen test reagent, thus leading to competition between both the antibodies, and by the competition, the sensitivity of the HBs antigen test reagent is reduced so that the detection of HBV by the test reagent is prevented.

DISCLOSURE OF THE INVENTION

Problem to be Solved by the Invention

The conventional HBs antigen test reagent using a monoclonal antibody to the common "a" determinant in the wild-type HBV cannot detect an escape mutant having a mutation on the common "a" determinant, and when blood judged to be negative by this test reagent is used in blood transfusion, infection with HBV may be caused. An object of the present invention is to develop a probe capable of detecting such escape mutant of HBV and a method of measuring HBs antigen by using the probe.

Another object of the present invention is to develop a probe which can measure HBs antigen without being prevented by a patient's antibody to the common "a" determinant even in an HBs antibody-positive sample from an infected patient, as well as a method of measuring HBs antigen by using the probe.

Means to Solve the Problem

The present inventors succeeded in solving the problem described above by using, as a probe, an antibody recognizing an epitope located on a peptide consisting of an amino acid sequence set forth in SEQ ID NO: 1.

That is, the present invention relates to a probe recognizing an epitope located on a peptide consisting of an amino acid sequence corresponding to positions 26 to 80 in hepatitis B virus s antigen and in particular to a probe recognizing an epitope located on a peptide consisting of an amino acid sequence in SEQ ID NO: 1.

The present invention also relates to a method of detecting hepatitis B virus or hepatitis B virus s antigen, which comprises using the probe described above.

In this specification, the positions of partial amino acid sequences in the HBs antigen composed of 226 amino acid residues are indicated by assigning number 1 to the N-terminal amino acid residue of the antigen. In an S region of HBV gene, there are Pre-S1, Pre-S2 and S genes coding for a large S protein composed of 389 to 400 amino acid residues governed by the Pre-S1 gene+Pre-S2 gene+S gene, a middle S protein composed of 281 amino acid residues governed by the Pre-S2 gene+S gene, and a small S protein composed of 226 amino acid residues governed by the S gene (Keiji Mitamura, "Nippon Rinsho, Bunshi Kan-En Uirusubyogaku, Kiso-Rinsho-Yobo" (Japanese Clinic, Molecular Hepatitis Virology, Fundamental-Clinic-Prophylaxis), Lower Volume, pp. 13-27, published on Oct. 26, 1995). The term "HBs antigen" used herein generally means the small S protein unless otherwise specified. However, the detection method of the present invention can detect all of large S protein, middle S protein and small S protein, and thus the hepatitis B virus antigen (HBs antigen) detected by the method contains the above 3 proteins.

The probe of the present invention is a probe capable of recognizing an epitope on a peptide consisting of the amino acid sequence set forth in SEQ ID NO: 1 and is typically a polyclonal or monoclonal antibody capable of specifically recognizing the epitope. Specific examples of the antibody are monoclonal antibodies produced by any of hybridoma cell strains 1C10, 4A3 and 6G6 deposited under Accession Nos. FERM ABP-10115, ABP-10116 and ABP-10117 since Sep. 9, 2004, with International Patent Organism Depositary (IPOD), National Institute of Advanced Industrial Science and Technology (AIST) at Central 6, 1-1-1, Higashi, Tsukuba City, Ibaraki Pref., Japan.

The amino acid sequence set forth in SEQ ID NO: 1 corresponds to an amino acid sequence in the positions 26 to 80 in the HBs antigen, that is, a hydrophilic region present in the inside of a lipid bilayer of HBs antigen. This epitope is positioned in the inside of HBV viral particle, small spherical particle or tubular particle, and unlike a region positioned in the side of ER lumen containing the common "a" determinant of HBs antigen, will not be subject to selective stress such as an external neutralizing antibody capable of inducing the escape mutant. Accordingly, a mutation on the above epitope, as compared with the common "a" determinant in the conventional method, will hardly undergo selective stress, and with the epitope of the present invention given, there would seldom or never occur the phenomenon wherein specific mutants only dominate such that only mutants not reacting with the HBs antigen measurement reagent are increased.

The probe of the present invention, when used to detect HBs antigen, hardly undergoes interference by a patient's antibody to HBs antigen. This is probably because the epitope recognized by the probe of the present invention is located in the inside of HBV particle, small spherical particle and tubular particle, so that as compared with the common "a" determinant of HBs antigen, this epitope is less likely to act as an immunogen in the body of the HBV-infected patient, and thus the production of patient's antibody to the epitope is suppressed.

By using the probe of the present invention, it is thus possible to reliably detect HBs antigen even in the escape mutant having a mutation on the common "a" determinant.

For detecting HBs antigen in HBV particle, small spherical particle or tubular particle in a sample with the probe of the present invention, an epitope on the amino acid sequence in positions 26 to 80 in HBs antigen, localized inside a lipid bilayer or in a spherical or tubular particle, should be in such a state as to be contacted with the probe.

Another aspect of the present invention is a method of detecting HBV or HBs antigen in a sample, which comprises adding to a sample a denaturant capable of denaturing a lipid bilayer or a protein aggregate, typically a protein denaturant such as a surfactant, chaotropic ion etc., particularly a surfactant in order to detect HBs antigen in the sample with the probe of the invention.

In the present invention, HBV particles, small spherical particles and tubular particles are denatured by using the denaturant, whereby their inside region consisting of the amino acid sequence in positions 26 to 80 in HBs antigen, that is, a hydrophilic region present in the inside of a lipid bilayer of HBs antigen, is exposed to the outside. The denaturant usable herein is a denaturant destroying lipid bilayers of HBV particles and breaking bonds (aggregation) among HBs antigens in small spherical particles and tubular particles but not inactivating the probe of the invention, and typically a surfactant such as sodium dodecyl sulfate can be used.

The present invention also provides a method of detecting HBV virus, which comprises using the probe of the present invention, a denaturant, and a probe capable of specifically recognizing HBV antigen other than HBs antigen, as well as a reagent for detection of HBV, having such a constitution, that is, comprising the probe of the present invention, a denaturant, and a probe capable of specifically recognizing HBV antigen other than HBs antigen.

By measuring HBV antigen other than HBs antigen, for example HBcr antigen (WO02/14871) with a probe used in combination with the probe of the present invention, a HBV patient sample which may be judged erroneously as being HBV-negative by detection of only HBs antigen can be grasped reliably as HBV-positive.

As described above, HBs antigen is known to undergo mutation at high frequency comparative to that of RNA virus. Accordingly, there is also a mutant HBs antigen consisting of a sequence which is different from the amino acid sequence of SEQ ID NO: 1 in the amino acid sequence in positions 26 to 80 in HBs antigen.

However, even HBs antigen having such a mutation can, if its amino acid sequence is specified, be expressed in *Escherichia coli* and purified according to the disclosure of this specification. A probe directed to such purified mutant HBs antigen is obtained and can be used to detect HBs antigen. In the present invention, therefore, the sequence corresponding to the amino acid sequence in positions 26 to 80 in HBs antigen is limited neither to a probe recognizing an epitope on the amino acid sequence shown in SEQ ID NO: 1 nor to the detection method of using said probe.

EFFECT OF THE INVENTION

By the probe of the present invention and a method of detecting HBV or HBs antigen by using the same, an escape mutant etc. having a mutation on common "a" determinant of HBs antigen, which cannot be detected by the conventional HBs antigen detection method, can be highly sensitively detected thereby highly reliably judging HBV infection. Even if a patient's antibody to the common "a" determinant of HBs antigen inhibits detection of HBs antigen, HBV infection can be reliably judged by the detection method of the present invention.

Even if a patient's antibody competing with the probe of the present invention occurs and inhibits detection of HBs antigen, HBV infection can be reliably judged by pretreatment with a combination of an acidifying agent or an alkalifying agent and a denaturant.

By using a combination of the probe of the invention and a probe recognizing another antigen of HBV to measure HBs antigen and another antigen of HBV simultaneously, HBV infection can be detected more reliably.

BEST MODE FOR CARRYING OUT THE INVENTION

The probe of the present invention can be any probe capable of specifically recognizing an epitope on a peptide consisting of an amino acid sequence corresponding to the positions 26 to 80 in HBs antigen, for example the amino acid sequence set forth in SEQ ID NO: 1, and typically an antibody, particularly a monoclonal antibody, raised against an antigen such as the above peptide or HBs antigen, is useful.

A peptide consisting of the amino acid sequence set forth in SEQ ID NO: 1 can be prepared by recombinant gene technology using a gene encoding the peptide or by chemical synthesis, and such preparation procedures can be attained by using various methods or instruments etc. known per se.

A gene fragment containing a nucleotide sequence encoding the amino acid sequence of SEQ ID NO: 1 can be prepared by separating virus genes from HBV patient serum and amplifying the objective gene by PCR. By using restriction enzyme sites derived from a linker added at the time of PCR, or restriction enzyme sites derived from a plasmid into which the gene fragment was inserted, the gene can be cloned into an expression vector.

This expression vector is transformed into a host such as *Escherichia coli*, and the *Escherichia coli* can be cultured to give HBs (26 to 80) antigen positioned in the inside of a lipid bilayer. Methods of collecting and purifying the objective protein from the microorganism thus obtained through culture can be achieved by conventional techniques, for example procedures such as sonicating disruption of cells, centrifugation, and various chromatographic techniques. That is, when the objective protein is efficiently expressed by the method described above, many proteins have formed inclusion bodies in the microorganism. By utilizing this feature, the microorganisms are suspended in a buffer under physiological conditions, such as physiological saline, then the cells are disrupted by sonication, and the disrupted microbial material is centrifuged to recover an insoluble fraction. The recovered insoluble fraction is extracted with 6 M urea and subjected to gel filtration to give high-purity trpE-HBs (26 to 80) antigen which can then be used as an immunogen.

The probe of the present invention, for example, the polyclonal antibody can be produced by periodically immunizing an animal such as rat, rabbit, goat or sheep, with the above-mentioned HBs (26 to 80) antigen or polypeptide (referred to hereinafter as the present antigen) alone or the present antigen conjugated to BSA, KLH or the like, as a mixture with an adjuvant such as Freund's complete adjuvant, and then collecting its serum. To obtain the polyclonal antibody having a specific recognition site, there is a method of using, as an immunogen, a partial peptide in the objective region.

Production of a monoclonal antibody by a hybridoma is well-known. For example, an animal such as BALB/c mouse is immunized periodically with the present antigen alone or a conjugate thereof with BSA, KLH or the like, as a mixture thereof with an adjuvant such as Freund's complete adjuvant. When the antibody titer in blood is increased, the present antigen is administered in final immunization to a caudal vein, and the spleen is aseptically excised, and the spleen cells are fused with suitable mouse myeloma cells to give hybridomas. This method can be carried out by the method of Kohler and Milstein (Nature 256:495-497, 1975).

The hybridoma obtained by the method described above is cultured in a suitable culture medium, and thereafter, a hybridoma cell producing an antibody showing specific reaction to the present antigen is selected and cloned. For cloning the antibody-producing hybridoma, not only limiting dilution but also a soft agar method (Eur J Immunol. 6:511-519, 1976) can be utilized. This hybridoma can be cultured in a medium or a mouse abdominal cavity to produce a monoclonal antibody in the medium or ascites.

The polyclonal antibody in serum or the monoclonal antibody produced in the medium or ascites can be purified by methods such as column chromatography on protein A. The polyclonal antibody can be subjected to methods such as affinity chromatography using a carrier-immobilized antigen, whereby only the antibody reacting with the specific antigen can be purified, and in a similar manner, the antibody not reacting with the specific antigen can also be obtained.

Besides the monoclonal antibody and polyclonal antibody, molecules used as the probe can be produced. For example, a recombinant antibody is described in detail in a review of Hoogenboon (Trends in Biotechnology, 15:62-70, 1997).

The denaturant used in the present invention may be any denaturant which can destroy the structure of a lipid bilayer of HBV particle or break bonds (aggregation) among HBs antigens in a small spherical particle and tubular particle consisting of HBs antigens. For example, urea, an acidifying agent and an alkalifying agent can be used, and particularly a surfactant is effective. The surfactant includes a nonionic surfactant, a cationic surfactant, an amphoteric surfactant and an anionic surfactant, any of which can be utilized insofar as it can destroy the structure of a lipid bilayer. For example, nonionic surfactants such as Tween 20 and Nonidet P-40 can sufficiently destroy the structure of a lipid bilayer, to expose the epitope in the present invention, although their surface activity is not so strong.

Anionic surfactants such as SDS and Sarcosyl are considered to have a strong surface activity, and such surfactants can also expose the epitope in the present invention. Treatment with the strong surfactant may destroy the conformational epitope of the protein so that an antibody recognizing the conformational epitope cannot bind to the antigen in a certain case; in this case, the antigen can be measured by using a probe recognizing the linear epitope of HBs antigen.

The denaturant plays a role not only of efficiently releasing HBs antigens present in a sample but also of binding the monoclonal antibody easily to HBs antigen.

In the present invention, use of a probe binding specifically to the antigen denatured with a surfactant as described above is particularly preferable. When an antibody is used as the probe, the antibody should be a probe capable of binding to the epitope in the invention exposed and denatured by the denaturation treatment described above.

For example, when a specific surfactant having a strong surface activity is used, it is necessary to select a monoclonal antibody against the epitope exposed and denatured by the surfactant. Accordingly, it is desired that a peptide consisting of the amino acid corresponding to positions 26 to 80 in HBs antigen (for example, a peptide consisting of the amino acid sequence set forth in SEQ ID NO: 1) subjected previously to denaturation treatment with the surfactant is used to immunize an animal, and also that the antibody is selected by using said peptide.

For screening of the antibody, the peptide antigen subjected to denaturation treatment is immobilized onto a solid phase and used in screening of a monoclonal antibody reacting with the antigen in a solution containing a surfactant, whereby the antibody of the invention suitable for immunoassay can be obtained. Since the screening solution contains a surfactant, a monoclonal antibody resistant to the denaturation action of the surfactant can be obtained.

The denaturant-treated HBs antigen in a sample can be detected with immunoassays such as enzyme-linked immunosorbent assay (ELISA), enzyme immunodot assay, radio-immunoassay, and assay based on agglutination or other well-known immunoassays. When a labeled antibody is used in detection, a label such as a fluorescence substance, chemiluminescent substance, radioactive substance or enzyme is used.

For example, when a method based on the principle of ELISA sandwich reaction is used in detecting HBs antigen in a sample, the method comprises the following steps. First, an antibody or the like recognizing the epitope located in the inside of a lipid bilayer is bound to a solid support (for example, an inner wall of a microtiter well). Then, blocking with bovine serum albumin or the like is carried out to prevent nonspecific reaction. A sample treated with a surfactant or the like is added to this support, to allow HBs antigen to be captured by the antibody immobilized thereon. A labeled antibody or the like to the captured HBs antigen can be reacted with the HBs antigen to detect it. The antibody to be bound to a solid support may be any antibody binding to the epitope positioned in the inside of a lipid bilayer. The labeled antibody may be any antibody binding to HBs antigen. Their combination is arbitrary, and a combination achieving high sensitivity and high specificity can be selected.

The usable solid support described above includes polystyrene, polycarbonate, polypropylene, a polyvinyl microtiter plate, a test tube, a capillary, beads (latex particles, erythrocytes, metal compounds etc.), a membrane (liposome etc.) and a filter and the like. The sample in which HBs antigen in the present invention can be measured includes biological body fluids such as whole blood, plasma, serum, urine, saliva and cerebrospinal fluid, as well as tissues such as hepatic tissues.

A method of treating HBs antigen in a sample in such a state as to be suitable for binding reaction with the probe, for example the monoclonal antibody, without involving complicated procedures is important in the present invention. That is, it is important that a lipid bilayer of HBs antigen contained in a sample is solubilized so that the epitope originally not exposed to the surfaces of virus particles becomes exposed.

EXAMPLES

The following examples are illustrative of the present invention, but are not intended to limit the scope of the present invention.

Example 1

Expression and Purification of TrpE-HBs (26 to 80) Antigen (A) Construction of TrpE-HBs (26 to 80) Antigen-Expressing Plasmid An expression plasmid for HBs (26 to 80) region was constructed by the following method. 100 µl serum from an HBV patient was mixed with 100 µl DNA extract [10 µl of 1 M Tris-HCl (pH 8.4), 8 µl of 250 mM EDTA, 40 µl of 10% SDS, 8 µl of 5 M NaCl, 10 µl of 20 mg/ml. Proteinase K, 1 µl tRNA (5 µg/µl), and 23 µl sterilized water] and incubated at 54° C. for 30 minutes. The sample was mixed with 200 µl phenol/chloroform (1/1) solution and then centrifuged at 15 Krpm for 5 minutes to give a supernatant, and 150 µl isopropanol and 7 µl of 5 M NaCl were added to the supernatant and left at −20° C. for 1 hour. After centrifugation at 15 Krpm at 4° C. for 5 minutes, the precipitates were rinsed with 70% ethanol and then centrifuged again at 15 Krpm at 4° C. for 5 minutes. The precipitates were air-dried and dissolved in 20 µl sterilized water to give an HBV DNA solution.

5 µl of this HBV DNA solution was subjected to PCR with 2 primers (that is, 5'-GAATTCCTCACAATACCACA-GAGTCTA-3' (SEQ ID NO: 2) and 5'-GGATCCT-TAAAAACGCCGCAGACACATCCAGCG-3' (SEQ ID NO: 3)). PCR was carried out with GeneAmp™ (DNA Amplification Reagent Kit manufactured by Perkin Elmer Cetus) under the conditions of DNA denaturation at 95° C. for 1 minute, annealing at 55° C. for 1 minute, and DNA synthesis at 72° C. for 1 minute, and the resulting DNA fragment was separated by 0.8% agarose gel electrophoresis and purified by a glass powder method (GeneClean). 0.5 µg of this amplified HBs (26 to 80) gene fragment was digested with 20 µl restriction enzyme reaction solution [50 mM Tris-HCl (pH7.5), 10 mM MgCl$_2$, 1 mM dithiothreitol, 100 mM NaCl, 15 U EcoRI enzyme and 15 U BamHI enzyme] at 37° C. for 1 hour and then subjected to 0.8% agarose gel electrophoresis to purify an about 180-bp EcoRI-BamHI fragment.

Then, 0.5 µg of DNA, that is, an expression vector pATtrpE, was digested with 20 µl restriction enzyme reaction solution [50 mM Tris-HCl (pH 7.5), 10 mM $MgCl_2$, 1 mM dithiothreitol, 100 mM NaCl, 15 U EcoRI enzyme and 15 U BamHI enzyme] at 37° C. for 1 hour, then 39 µl water was added to the reaction solution which was then heat-treated at 70° C. for 5 minutes, and 1 µl (250 U/µl) of bacteria alkaline phosphatase (BAP) was added thereto and incubated at 37° C. for 1 hour.

This reaction solution was subjected to extraction with phenol, and the resulting aqueous phase was precipitated with ethanol, and the precipitates were dried. 0.5 µg of the resulting EcoRI-BamHI-treated vector DNA and the above-mentioned 180-bp HBs (26 to 80) fragment were added to a mixture prepared by 1 µl (350 U/µl) T4 ligase to 5 µl of a 10× ligase buffer [660 mM Tris-HCl (pH 7.5), 66 mM $MgCl_2$, 100 mM dithiothreitol, 1 mM ATP] and then adjusting it to 501 with water, and then incubated at 16° C. overnight to effect ligation reaction. To obtain the expression plasmid pATtrpE-HBs (26 to 80), this ligation reaction solution was used to transform *Escherichia coli* HB101.

The competent *Escherichia coli* strain used in transformation is produced by a calcium chloride method [Mandel, M. and Higa, A., J. Mol. Biol., 53, 159-162 (1970)]. The transformed *Escherichia coli* was plated onto an LB plate (1% tryptone, 0.5% NaCl, 1.5% agar) containing 25 µg/ml ampicillin and incubated at 37° C. overnight. A transformed bacterial colony occurring on the plate was transferred via a platinum loop to an LB medium containing 25 µg/ml ampicillin and cultured overnight at 37° C.

1.5 ml of the transformed bacterial culture was centrifuged to collect the bacteria, and mini-preparation of plasmid DNA was carried out by the alkali method [Manniatis et al., Molecular Cloning: A Laboratory Manual, (1982)]. 1 µg of the resulting plasmid DNA was digested with 20 µl restriction enzyme reaction solution [50 mM Tris-HCl (pH7.5), 10 mM $MgCl_2$, 1 mM dithiothreitol, 100 mM NaCl, 15 U EcoRI enzyme and 15 U BamHI enzyme] at 37° C. for 1 hour and then subjected to agarose gel electrophoresis to separate pATtrpE-HBs (26 to 80) expression plasmid generating about 180-bp EcoRI-BamHI fragment.

(B) Expression and Purification of TrpE-HBs (26 to 80) Antigen

The *Escherichia coli* HB101 strain harboring the expression plasmid pATtrpE-HBs (26 to 80) was inoculated onto 3 ml of 2YT medium (1.6% tryptone, 1% yeast extract, 0.5% NaCl) containing 50 µg/ml ampicillin, and then cultured at 37° C. for 9 hours. 1 ml of this culture was inoculated into 100 ml M9-CA medium (0.6% $Na_2HPO_4$, 0.5% $KH_2PO_4$, 0.5% NaCl, 0.1% $NH_4Cl$, 0.1 mM $CaCl_2$, 2 mM $MgSO_4$, 0.5% casamino acid, 0.2% glucose) containing 50 µg/ml ampicillin, and then cultured at 37° C. Indol-acrylic acid was added to a final concentration of 40 mg/l when $OD_{600}$ reached 0.3, and further cultured for additional 16 hours. This culture was centrifuged at 5 Krpm for 10 minutes to collect the microorganism.

The microorganism was suspended in 20 ml buffer A [50 mM Tris-HCl (pH 8.0), 1 mM EDTA, 30 mM NaCl] and then centrifuged again to give 2.6 g expression microorganism. The resulting microorganism was suspended in 10 ml buffer A and then the *E. coli* membrane was disrupted by sonication, followed by centrifugation to give an insoluble fraction containing a trpE-HBs (26 to 80) fusion antigen.

This insoluble fraction was dissolved in 3 ml PBS containing 8 M urea, 10 mM dithiothreitol and 1 mM EDTA and subjected to gel filtration through a Sephacryl S300HR column in the presence of 6 M urea, whereby the trpE-HBs (26 to 80) fusion antigen to almost homogeneity.

Example 2

Preparation of Hybridoma

The polypeptide [trpE-HBs (26 to 80)] prepared by the method described above was dissolved with 6M urea and then diluted at a final concentration of 0.2 to 1.0 mg/ml in 10 mM phosphate buffer (pH 7.3) containing 0.15 M NaCl (PBS), then mixed with an equal volume of Freund's adjuvant, and administered intraperitoneally in a dose of 10 to 20 µg to a 4- to 6-week-old BALB/c mouse.

Booster was carried out every 2 to 4 weeks in the same manner as above, and for final immunization, 10 µg HBs dissolved in PBS was administered to the caudal vein.

At three days after the final immunization, the spleen was aseptically removed from the mouse, then broken into individual cells with scissors and a metallic mesh and washed 3 times with RPMI-1640 medium. Mouse myeloma cell strain Sp2/OAg14 at the logarithmic growth phase was washed 3 times with RPMI-1640 medium, and the cells were mixed with the spleen cells at a ratio of 1:5. After centrifugation at 200×g for 5 minutes, the supernatant was removed, and 1 ml RPMI-1640 medium containing 50% polyethylene glycol (PEG) 4000 (Merck) was added slowly to the cell mass under gentle mixing, and 10 ml RPMI-1640 medium was further added thereby effecting cell fusion.

The resultant fusion cells were centrifuged (200×g, 5 minutes) to remove PEG and then suspended in RPMI-1640 medium containing 10% fetal bovine serum and hypoxanthine, aminopterin and thymidine (HAT) and plated onto a 96-well cell culture plate. After hybridomas only were proliferated by culture for about 10 days, clones producing the objective antibody were selected by the ELISA method to give hybridomas producing the monoclonal antibody having desired reaction specificity.

The resulting hybridomas were made monoclonal by limiting dilution to establish antibody-producing hybridomas. The resulting hybridomas were designated 6G6, 4A3, and 1C10, respectively. These hybridoma cells have been deposited since Sep. 9, 2004, with International Patent Organism Depositary (IPOD), National Institute of Advanced Industrial Science and Technology (AIST), Japan.

Example 3

Preparation and Analysis of Monoclonal Antibody

Each of the hybridomas obtained by the method described in Example 2 was transplanted in a BALB/c mouse abdominal cavity previously administered with pristane, and the monoclonal antibody produced in the ascites was obtained.

The IgG fraction containing the monoclonal antibody was purified by affinity chromatography on a protein A Sepharose column.

The respective obtained monoclonal antibodies were analyzed for their target epitope by using the TrpE-HBs (26 to 80) antigen and synthetic peptides each consisting of 20 amino acids synthesized on the basis of a sequence derived from the HBs region, and as a result, it was found that as shown in Table 1, these monoclonal antibodies recognize an epitope (amino acid numbers: 26 to 80) of the HBs antigen, which is located in the inside of a lipid bilayer.

[Table 1]

TABLE 1

| (Poly)peptide name | Amino acid number | Monoclonal antibody name | | |
|---|---|---|---|---|
| | | 4A3 | 6G6 | 1C10 |
| HBS-1 | 1-20 | − | − | − |
| HBS-2 | 11-30 | − | − | − |
| HBS-3 | 21-40 | − | − | − |
| HBS-4 | 31-50 | + | − | − |
| HBS-5 | 41-60 | − | + | − |
| HBS-6 | 51-70 | − | + | + |
| HBS-7 | 61-80 | − | − | − |
| HBS-8 | 71-90 | − | − | − |
| TrpE-HBs(26-80) | 26-80 | + | + | + |

By an isotyping kit (Zymed) using anti-mouse Ig isotype antibodies, (sub)classes of the respective monoclonal antibodies were identified. As a result, the subtype of 6G6 and 4A3 was IgG1, κ, and the subtype of 1C10 was IgG2a, κ, as shown in Table 2.

There is no report on an antibody recognizing an antigen epitope present in the region of amino acid numbers 31 to 70 in the present invention, and it was found that the monoclonal antibodies 6G6, 4A3, and 1C10 recognize the novel epitope respectively.

[Table 2]

TABLE 2

| Clone name | Subclass | Estimated recognition site (amino acid number) |
|---|---|---|
| 4A3 | IgG1, κ | 31-50 |
| 6G6 | IgG1, κ | 51-60 |
| 1C10 | IgG2a, κ | 51-70 |

Example 4

Examination of the Detection Method Using a Surfactant

The anti-HBs antigen monoclonal antibody 6G6 was diluted to a final concentration of 6 μg/ml with 10 mM sodium phosphate buffer (pH 7.3) containing 0.15 M NaCl and then pipetted onto a 96-well microtiter plate (Nunc) in a volume of 80 μl per well. The plate was left at 4° C. overnight and then washed twice with 0.35 ml of 10 mM sodium phosphate buffer (pH 7.3) containing 0.15 M NaCl, followed by adding 0.35 ml of 10 mM sodium phosphate buffer (pH 7.3) containing 0.5% casein-Na (referred to hereinafter as blocking solution) and further incubated at room temperature for 2 hours.

After the blocking solution was removed, 40 μl of 100 mM sodium phosphate buffer (pH 7.3) containing 0.15 M NaCl, 1% BSA, and 0.5% casein-Na, to which various surfactants had been added at a final concentration of 4% or 8%, and 40 μl of measurement sample, were added to each well, then reacted at room temperature for 1 hour, washed 5 times with 0.35 ml washing solution, followed by adding 80 μl monoclonal antibody (5C3) labeled with peroxidase (POD) and reacting the mixture at room temperature for 30 minutes. Each well was washed 6 times with 0.35 ml of the washing solution, and after reaction thereof with 80 μl of a substrate (orthophenylene diamine referred to hereinafter as OPD) solution at room temperature for 30 minutes, 80 μl of 2 N sulfuric acid solution was added to each well which was then measured for its absorbance at a wavelength of 492 nm ($OD_{492}$) with its absorbance at a wavelength of 630 nm as the reference.

The results of measurement of HBs-positive serum with various surfactants are shown in Table 3. When the surfactant-free buffer was used to measure HBs antigen-positive serum, HBs antigen could not be detected, but when the buffers containing various kinds of surfactants (anionic, cationic, amphoteric and nonionic surfactants) were used in the measurement, a sufficient signal could be obtained to clearly detect HBs antigen. It was thereby revealed that a novel epitope present in the inside of a lipid bilayer of HBs antigen could be detected by exposing the epitope to the outside with various surfactants.

5C3, the monoclonal antibody labeled with peroxidase, is a monoclonal antibody obtained by expressing an antigen consisting of an amino acid sequence in the positions 1 to 226, that is, the full-length HBs antigen, then purifying this recombinant antigen and immunizing a mouse with it. It was confirmed that the antibody 5C3 thus obtained binds to the above recombinant HBs antigen. However, when synthetic peptides each consisting of 20 amino acids overlapping with each other by 10 amino acids were synthesized on the basis of the amino acid sequence in positions 1 to 226 in the HBs antigen and examined for their binding to the antibody 5C3 by the same method as in Example 3, the antibody 5C3 did not react with any of the synthetic peptides. Accordingly, it is estimated that the antibody 5C3 recognizes not a linear epitope of an amino acid sequence of HBs antigen, but a conformational epitope thereof.

[Table 3]

TABLE 3

| Reagent name | Polarity | Concentration (%) | Negative serum | Positive serum 1 | Positive serum 2 |
|---|---|---|---|---|---|
| No addition (control) | — | — | 0.004 | 0.005 | 0.010 |
| C10TAC | cationic | 8 | 0.008 | 0.579 | 0.451 |
| C14TAC | cationic | 8 | 0.025 | 2.222 | 1.466 |
| Lauryl pyridinium chloride | cationic | 8 | 0.026 | 0.145 | 0.121 |
| Tween20 | nonionic | 8 | 0.006 | 0.552 | 0.541 |
| Triton X100 | nonionic | 8 | 0.004 | 0.895 | 0.629 |
| NP40 | nonionic | 8 | 0.005 | 0.640 | 0.528 |
| MEGA10 | nonionic | 8 | 0.012 | 1.051 | 0.738 |
| Brij35 | nonionic | 8 | 0.011 | 1.003 | 0.811 |
| CHAPS | amphoteric | 8 | 0.015 | 0.053 | 0.040 |
| C12APS | amphoteric | 4 | 0.007 | 1.523 | 1.232 |
| Sarcosyl | anionic | 4 | 0.010 | 1.990 | 1.833 |
| SDS | anionic | 4 | 0.029 | 1.401 | 1.198 |
| No addition (control) | — | — | 0.014 | 0.019 | 0.021 |
| C12TAB | cationic | 4 | 0.020 | 0.949 | 0.689 |
| C14APS | amphoteric | 4 | 0.014 | 2.857 | 2.911 |
| C16APS | amphoteric | 4 | 0.013 | 2.829 | 2.870 |
| C18APS | amphoteric | 4 | 0.013 | 2.806 | 2.698 |
| C8SO3 | anionic | 4 | 0.016 | 0.740 | 0.223 |
| C11SO3 | anionic | 4 | 0.048 | 2.912 | 2.922 |
| Sodium hexadecyl-sulfate | anionic | 4 | 0.010 | 0.397 | 0.139 |

Example 5

Measurement of HBs Antigen-Negative Sample

The HBs antigen in a sample which was HBs antigen-negative but was suspected of infection with HBV was measured by a modification to the method in Example 4.

The anti-HBs antigen monoclonal antibody 6G6 was diluted to a final concentration of 6 μg/ml with 10 mM sodium phosphate buffer (pH 7.3) containing 0.15 M NaCl and then pipetted onto a 96-well microtiter plate (Nunc) in a volume of 100 μl per well. The plate was left at 4° C. overnight and then washed twice with 0.35 ml of 10 mM sodium phosphate buffer (pH 7.3) containing 0.15 M NaCl, followed by adding 0.35 ml of 10 mM sodium phosphate buffer (pH 7.3) containing 0.5% casein sodium and 3% sucrose (blocking solution) and leaving the mixture at room temperature for 2 hours.

After the blocking solution was removed, 50 μl of 100 mM sodium phosphate buffer (pH 7.0) containing 0.15 M NaCl, 10 mM EDTA-2Na, 0.2% proclin, 1% BSA, 0.1% casein sodium, 3% horse serum, 2% mouse serum and 10% Brij 35, and 50 μl measurement sample, were added to each well, reacted at room temperature for 1 hour, washed 5 times with 0.35 ml washing solution, followed by adding 100 μl of the monoclonal antibody (5C3) labeled with peroxidase (POD) and reacting the mixture at room temperature for 30 minutes.

After the reaction, each well was washed 6 times with 0.35 ml of the washing solution, and after reaction thereof with 100 μl solution of a substrate (orthophenylene diamine referred to hereinafter as OPD) at room temperature for 30 minutes, 2 N sulfuric acid solution was added to the sample which was then measured for its absorbance at a wavelength of 492 nm ($OD_{492}$) with its absorbance at a wavelength of 630 nm as the reference.

The sample used was a sample purchased from IIC Japan; the HBs antigen and anti-HBs antibody were measured by the CLIA method of Abbott Laboratories; and HBN-DNA was measured by the TMA method of Gen-Probe Incorporated.

[Table 4]

three anti-HBs antibody-containing HBV antigen-positive samples (#990493, #990640, #990650) and then incubated at room temperature for 10 minutes, and 50 μL solution of the mixture was examined as a measurement sample by the following method.

The anti-HBs antigen monoclonal antibody 6G6 was diluted to a final concentration of 6 μg/ml with 10 mM phosphate buffer (pH 7.3) containing 0.15 M NaCl and then pipetted onto a 96-well microtiter plate (Nunc) in a volume of 100 μl per well. The plate was incubated at 4° C. overnight.

The plate was washed twice with 10 mM phosphate buffer (pH 7.3) containing 0.15 M NaCl, followed by adding 350 μl of 10 mM phosphate buffer, pH 7.1, containing 0.5% casein sodium and incubating the plate for 2 hours. After the blocking solution was removed, 100 μl reaction buffer containing a neutralizing agent and each of the various measurement samples obtained by the sample treatment method were added to the respective wells, reacted at room temperature for 2 hours under shaking, washed 6 times with 350 μl of 10 mM phosphate buffer, pH 7.3, containing 0.05% Tween 20 (washing solution), followed by adding 100 μL of the monoclonal antibody (5C3) labeled with peroxidase (POD) and reacting the mixture at room temperature for 30 minutes. Each well was washed 6 times with the washing solution and then incubated with 100 μl solution of a substrate (orthophenylene diamine referred to hereinafter as OPD) for 30 minutes, and then 100 μl of 2 N sulfuric acid solution was added to each well which was then measured for its absorbance at a wavelength of 492 nm ($OD_{492}$) with its absorbance at a wavelength of 630 nm as the reference. The hydrochloric acid concentra-

TABLE 4

| No. | HBV-DNA TMA LGE/ml | HBsAg (measurement method of the invention) 6G6/5C3 Mean | Judgment | HBsAg CLIA IU/ml | Judgment | HBsAb CLIA mIU/ml | Judgment | HBeAg | HBeAb | HBcAb | HBcrAg HB44+/92 RLI | Judgment |
|---|---|---|---|---|---|---|---|---|---|---|---|---|
| 1 | 6.1 | 2.772 | + | 2.28 | + | 115.7 | + | − | + | + | 965,534 | + |
| 2 | 6.7 | 2.819 | + | 0.02 | − | 541.8 | + | − | + | + | 152,531 | + |
| 3 | 6.6 | 0.005 | − | 0.01 | − | 773.0 | + | − | + | + | 252,891 | + |
| 4 | 6.8 | 2.646 | + | 1.42 | + | 174.1 | + | − | + | + | 337,807 | + |
| 5 | 6.4 | 2.682 | + | 0.01 | − | 545.6 | + | − | + | + | 312,615 | + |

The 5 samples shown in Table 4 are HBV-DNA-positive by the TMA method. The samples are also HBs antibody-positive by the CLIA method of Abbott Laboratories and considered to be serum from patients infected with HBV. However, the samples Nos. 2, 3 and 5 were judged to be negative by the HBsAg CLIA method of Abbott Laboratories, that is, the conventional HBs antigen measuring method.

When these three HBs antigen-negative samples were judged by the method of the present invention, HBs antigen could be detected in the samples Nos. 2 and 5. The sample No. 3 judged to be HBs antigen-negative by both the measurement method of the present invention and the HBsAg CLIA measurement method of Abbott Laboratories could be detected by the HBcrAg measurement method, and the simultaneous measurement of HBs antigen and HBcr antigen is useful in more accurate detection of HBV antigen.

Example 6

1) Concentration of an Acidifying Agent

50 μL aqueous hydrochloric acid at various concentrations was added to 50 μL of an HBV antigen-negative sample or tion shown in the table is the concentration during treatment after mixing the sample with the treatment agent.

Even by incubation of anti-HBs antibody-containing HBs antigen-positive samples (#990493, #990640, #990650) at room temperature for 10 minutes with the hydrochloric acid-free solution, HBs antigen activity could hardly be detected. HBs antigen activity was recognized at a concentration from 0.05 N hydrochloric acid at the time of treatment and reached a peak at a concentration of 0.25 to 1.0 N (Table 5).

[Table 5]

TABLE 5

| HCl Concentration (N) | HBV negative sample Serum from healthy person | HBV positive sample | | |
|---|---|---|---|---|
| | | #990493 | #990640 | #990650 |
| 0 | 0.002 | 0.002 | 0.002 | 0.005 |
| 0.05 | 0.003 | 0.210 | 0.045 | 0.163 |
| 0.1 | 0.003 | 0.425 | 0.055 | 0.223 |

TABLE 5-continued

| HCl Concentration (N) | HBV negative sample Serum from healthy person | HBV positive sample | | |
|---|---|---|---|---|
| | | #990493 | #990640 | #990650 |
| 0.25 | 0.001 | 0.565 | 0.079 | 0.369 |
| 0.5 | 0.001 | 0.541 | 0.097 | 0.301 |
| 0.75 | 0.000 | 0.550 | 0.100 | 0.393 |
| 1 | 0.003 | 0.450 | 0.085 | 0.333 |
| 1.5 | 0.003 | 0.550 | 0.084 | 0.281 |

Example 7

2) Various Surfactants in the Presence of an Acidifying Agent

30 µL of each of various surfactants dissolved in 1.0 N aqueous hydrochloric acid was added to 30 µL of an HBV antigen-negative samples or HBs antigen-positive samples (#990493, #990640, #990650) and then incubated at room temperature for 10 minutes, and 50 µL solution of the mixture was examined as a measurement sample by the method described in 1) (Tables 6 to 9). The hydrochloric acid concentration and surfactant concentration shown in the tables are the concentrations during treatment after mixing the sample with the treating agent.

As shown in Tables 6 to 9, the surfactant with which at least 1 of the 3 samples had shown higher reactivity than the judgment criteria of each sample was judged to be an effective surfactant. As a result, it was found that when various surfactants were added together with an acidifying agent such as hydrochloric acid or sulfuric acid, there was a surfactant with which the immunoreactivity of the HBs antigen in the HBs antigen-positive sample was increased. The surfactant judged to be effective was an amphoteric or cationic surfactant having, in its molecule, a straight-chain alkyl group and a tertiary amine or quaternary ammonium salt.

Nonionic surfactants such as Triton X100 and Bridj 35 are also recognized to be effective. A surfactant having a steroid skeleton, such as CHAPS, did not show improvement in reactivity. In addition, anionic surfactants such as SDS and sodium N-lauroyl sarcosinate, and deoxycholic acid, were also examined, but these were poor in solubility in the presence of an acidifying agent, thus making their examination infeasible.

An increase in measurement sensitivity was recognized by adding an amphoteric or cationic surfactant having, in its molecule, a straight-chain alkyl group and a tertiary amine or a quaternary ammonium salt to an acidifying agent. Such surfactant effective in the presence of an acidifying agent in the treatment solution, when used in the treatment solution without the acidifying agent, reduced the measurement sensitivity significantly. From the foregoing, the reason for the increase in measurement sensitivity would be that the anti-HBs antibody acting as a factor inhibiting detection of HBs antigen is inactivated by the acidifying agent, while the epitope located inside a lipid bilayer of HBs antigen in a sample is exposed to the outside by adding the surfactant, thus significantly improving the reactivity thereof with 6G6.

[Table 6]

TABLE 6

| | Cationic (TAC type) | | | |
|---|---|---|---|---|
| | Concentration (%) | HBV negative sample Serum from healthy person | HBV positive sample | | |
| | | | #990493 | #990640 | #990650 |
| No addition | 0 | 0.006 | 0.541 | 0.097 | 0.254 |
| Criteria for judging the effect of surfactant | | | 0.812 | 0.146 | 0.381 |
| Surfactant added to 0.5N HCl | | | | | |
| Octyltrimethyl-ammonium Chloride [$CH_3(CH_2)_7N(CH_3)_3$]Cl | 0.5 | 0.014 | 0.648 | 0.146 | 0.268 |
| | 1 | 0.018 | 0.783 | 0.194 | 0.327 |
| | 2 | 0.019 | 0.898 | 0.272 | 0.348 |
| | 5 | 0.012 | 1.285 | 0.419 | 0.624 |
| Decyltrimethyl-ammonium Chloride [$CH_3(CH_2)_9N(CH_3)_3$]Cl | 0.5 | 0.020 | 0.727 | 0.231 | 0.288 |
| | 1 | 0.022 | 0.976 | 0.346 | 0.422 |
| | 2 | 0.011 | 1.232 | 0.391 | 0.525 |
| | 5 | 0.004 | 1.602 | 0.419 | 0.675 |
| Dodecyltrimethyl-ammonium Chloride [$CH_3(CH_2)_{11}N(CH_3)_3$]Cl | 0.5 | 0.034 | 0.797 | 0.261 | 0.324 |
| | 1 | 0.030 | 0.941 | 0.303 | 0.386 |
| | 2 | 0.024 | 0.972 | 0.259 | 0.415 |
| | 5 | 0.006 | 0.990 | 0.234 | 0.392 |
| Tetradecyltri-methylammonium Chloride [$CH_3(CH_2)_{13}N(CH_3)_3$]Cl | 0.5 | 0.029 | 0.924 | 0.261 | 0.357 |
| | 1 | 0.035 | 1.002 | 0.306 | 0.436 |
| | 2 | 0.015 | 1.032 | 0.216 | 0.409 |
| | 5 | 0.005 | 0.804 | 0.136 | 0.281 |
| Hexadecyltri-methylammonium Chloride | 0.5 | 0.032 | 0.933 | 0.254 | 0.425 |
| | 1 | 0.031 | 0.974 | 0.271 | 0.458 |
| | 2 | 0.021 | 0.977 | 0.206 | 0.402 |

TABLE 6-continued

| Cationic (TAC type) | | | | |
|---|---|---|---|---|
| | Concentration (%) | HBV negative sample Serum from healthy person | HBV positive sample | |
| | | | #990493 | #990640 | #990650 |

TABLE 6-continued

| | | HBV negative sample Serum from healthy | HBV positive sample | | |
|---|---|---|---|---|---|
| | Concentration (%) | person | #990493 | #990640 | #990650 |
| $[CH_3(CH_2)_{15}N(CH_3)_3]Cl$ | 5 | 0.005 | 0.811 | 0.164 | 0.279 |
| Lauryl pyridinium | 0.5 | 0.021 | 0.587 | 0.190 | 0.228 |
| Chloride | 1 | 0.013 | 0.716 | 0.236 | 0.309 |
| $[C_5H_5NCH_2(CH_2)_{10}CH_3]Cl$ | 2 | 0.001 | 0.896 | 0.211 | 0.312 |
| | 5 | 0.001 | 0.847 | 0.168 | 0.249 |

[Table 7]

TABLE 7

| | | HBV negative sample Serum from healthy | HBV positive sample | | |
|---|---|---|---|---|---|
| Cationic (TAB type) | Concentration (%) | person | #990493 | #990640 | #990650 |
| No addition | 0 | 0.013 | 0.569 | 0.097 | 0.286 |
| Criteria for judging the effect of surfactant Surfactant added to 0.5N HCl | | | 0.854 | 0.146 | 0.429 |
| Octyltrimethylammonium Bromide $[CH_3(CH_2)_7N(CH_3)_3]Br$ | 0.5 | 0.019 | 0.713 | 0.128 | 0.301 |
| | 1 | 0.022 | 0.836 | 0.165 | 0.347 |
| | 2 | 0.025 | 0.968 | 0.202 | 0.361 |
| | 5 | 0.012 | 1.381 | 0.314 | 0.639 |
| Decyltrimethylammonium Bromide $[CH_3(CH_2)_9N(CH_3)_3]Br$ | 0.5 | 0.025 | 0.788 | 0.183 | 0.306 |
| | 1 | 0.026 | 1.051 | 0.260 | 0.462 |
| | 2 | 0.008 | 1.535 | 0.320 | 0.588 |
| | 5 | 0.005 | 1.784 | 0.465 | 0.800 |
| Dodecyltrimethyl-ammonium Bromide $[CH_3(CH_2)_{11}N(CH_3)_3]Br$ | 0.5 | 0.029 | 0.938 | 0.205 | 0.353 |
| | 1 | 0.037 | 1.153 | 0.303 | 0.445 |
| | 2 | 0.028 | 1.343 | 0.309 | 0.544 |
| | 5 | 0.011 | 1.402 | 0.317 | 0.496 |
| Tetradecyltrimethyl-ammonium Bromide $[CH_3(CH_2)_{13}N(CH_3)_3]Br$ | 0.5 | 0.034 | 0.994 | 0.210 | 0.366 |
| | 1 | 0.041 | 1.181 | 0.284 | 0.467 |
| | 2 | 0.020 | 1.272 | 0.237 | 0.443 |
| | 5 | 0.007 | 1.201 | 0.289 | 0.443 |
| Hexadecyltrimethyl-ammonium Bromide $[CH_3(CH_2)_{15}N(CH_3)_3]Br$ | 0.5 | 0.034 | 1.080 | 0.208 | 0.429 |
| | 1 | 0.037 | 1.196 | 0.236 | 0.498 |
| | 2 | 0.037 | 1.321 | 0.226 | 0.472 |
| | 5 | 0.005 | 1.017 | 0.179 | 0.414 |

[Table 8]

TABLE 8

| | | Amphoteric | | | |
|---|---|---|---|---|---|
| | Concentration | HBV negative sample Serum from healthy | HBV positive sample | | |
| | (%) | person | #990493 | #990640 | #990650 |
| No addition | 0 | 0.008 | 0.533 | 0.097 | 0.240 |
| Criteria for judging the effect of surfactant Surfactant added to 0.5N HCl | | | 0.799 | 0.146 | 0.359 |
| 3-[3-(Cholamidopropyl) dimethyl-ammonio]-1-propanesulfonate | 0.5 | 0.009 | 0.606 | 0.115 | 0.248 |
| | 1 | 0.007 | 0.635 | 0.125 | 0.302 |
| | 2 | 0.001 | 0.547 | 0.076 | 0.246 |
| | 5 | 0.000 | 0.456 | 0.040 | 0.184 |
| N-Dodecyl-N,N-dimethyl-3-ammonio-1-propanesulfonate $CH_3(CH_2)_{11}N(CH_3)_2[(CH_2)_3SO_3]$ | 0.5 | 0.013 | 0.807 | 0.189 | 0.379 |
| | 1 | 0.009 | 1.073 | 0.246 | 0.455 |
| | 2 | 0.002 | 1.296 | 0.302 | 0.651 |
| | 5 | 0.000 | 1.365 | 0.410 | 0.695 |
| N-Tetradecyl-N,N-dimethyl-3-ammonio-1-propanesulfonate $CH_3(CH_2)_{13}N(CH_3)_2[(CH_2)_3SO_3]$ | 0.5 | 0.012 | 0.873 | 0.181 | 0.386 |
| | 1 | 0.010 | 1.076 | 0.245 | 0.477 |
| | 2 | 0.005 | 1.267 | 0.268 | 0.554 |
| | 5 | 0.000 | 1.362 | 0.356 | 0.558 |
| N-Hexadecyl-N,N-dimethyl-3-ammonio-1-propanesulfonate $CH_3(CH_2)_{15}N(CH_3)_2[(CH_2)_3SO_3]$ | 0.5 | 0.015 | 1.013 | 0.209 | 0.502 |
| | 1 | 0.016 | 1.233 | 0.287 | 0.581 |
| | 2 | 0.014 | 1.290 | 0.256 | 0.575 |
| | 5 | 0.002 | 1.286 | 0.276 | 0.519 |

[Table 9]

TABLE 9

| | | Nonionic | | | |
|---|---|---|---|---|---|
| | Concentration | HBV negative sample Serum from healthy | HBV positive sample | | |
| | (%) | person | #990493 | #990640 | #990650 |
| No addition | 0 | 0.005 | 0.459 | 0.070 | 0.210 |
| Criteria for judging the effect of surfactant Surfactant added to 0.5N HCl | | | 0.689 | 0.105 | 0.315 |
| Triton X-100 | 0.5 | 0.011 | 0.545 | 0.117 | 0.284 |
| | 1 | 0.009 | 0.675 | 0.163 | 0.356 |
| | 2 | 0.007 | 0.790 | 0.193 | 0.344 |
| | 5 | 0.003 | 0.827 | 0.201 | 0.382 |
| Triton X-114 | 0.5 | 0.006 | 0.470 | 0.112 | 0.283 |
| | 1 | 0.005 | 0.554 | 0.149 | 0.372 |
| | 2 | 0.003 | 0.678 | 0.160 | 0.370 |
| | 5 | 0.001 | 0.489 | 0.118 | 0.258 |
| Tween 20 | 0.5 | 0.009 | 0.437 | 0.086 | 0.251 |
| | 1 | 0.007 | 0.468 | 0.110 | 0.278 |
| | 2 | 0.008 | 0.647 | 0.118 | 0.341 |
| | 5 | 0.007 | 0.605 | 0.147 | 0.307 |
| Tween 80 | 0.5 | 0.007 | 0.339 | 0.063 | 0.209 |
| | 1 | 0.007 | 0.312 | 0.068 | 0.220 |
| | 2 | 0.009 | 0.451 | 0.051 | 0.245 |
| | 5 | 0.007 | 0.498 | 0.063 | 0.240 |

TABLE 9-continued

| | | Nonionic | | | |
|---|---|---|---|---|---|
| | Concentration | HBV negative sample Serum from healthy | HBV positive sample | | |
| | (%) | person | #990493 | #990640 | #990650 |
| Bridj 35 | 0.5 | 0.010 | 0.496 | 0.076 | 0.241 |
| | 1 | 0.010 | 0.526 | 0.097 | 0.291 |
| | 2 | 0.011 | 0.704 | 0.108 | 0.374 |
| | 5 | 0.020 | 0.907 | 0.173 | 0.434 |

Example 8

3) Protein Denaturant in the Presence of an Acidifying Agent

30 L protein denaturant (urea or guanidine hydrochloride) dissolved in 1.0 N aqueous hydrochloric acid was added to 30 μL of an HBV-negative sample or three HBs antigen positive samples (#990493, #990640, #990650) and then incubated at room temperature for 10 minutes, and 50 μL solution of the mixture was examined as a measurement sample by the method described in 1). The immunoreactivity of each HBs antigen-positive sample is shown in Table 10. The hydrochloric acid concentration and protein denaturant concentration shown in Table 10 are the concentrations during treatment after mixing the sample with the treatment agent.

The samples showed higher immunoreactivity with the protein denaturant in the presence of the acidifying agent than with the acidifying agent only; that is, the immunoreactivity was increased about 1.5- to 3-fold with urea or about 2- to 3-fold with guanidine hydrochloride. At the time of treatment with the acidifying agent, serum protein or the like may be denatured to cause precipitation or to become turbid in some cases so that the pipetting procedure is hindered and precipitates are often a major cause of giving a false-positive result. There may also occur a reduction in sensitivity attributable to incorporation of the objective antigen into such precipitates. It was revealed that formation of such precipitates can be significantly reduced by adding urea or guanidine hydrochloride at a concentration of 0.5 M or more at the time of treatment, and this effect is made particularly higher by adding urea at a concentration of 1.5 to 4 M and guanidine hydrochloride at a concentration of 2 to 3.5 M at the time of treatment.

[Table 10]

TABLE 10

| | Concentration (M) | HBV negative sample Serum from healthy person | HBV positive sample #990493 | #990640 | #990650 |
|---|---|---|---|---|---|
| No addition Protein denaturant added to 0.5N HCl | 0 | 0.018 | 0.483 | 0.076 | 0.175 |
| Urea | 0.5 | 0.015 | 0.555 | 0.085 | 0.204 |
| | 1 | 0.010 | 0.619 | 0.076 | 0.236 |
| | 1.5 | 0.006 | 0.636 | 0.090 | 0.248 |
| | 2 | 0.005 | 0.686 | 0.081 | 0.293 |
| | 2.5 | 0.005 | 0.725 | 0.100 | 0.335 |
| | 3 | 0.005 | 0.771 | 0.088 | 0.382 |
| | 3.5 | 0.003 | 0.830 | 0.116 | 0.443 |
| | 4 | 0.008 | 1.041 | 0.143 | 0.578 |
| Guanidine-HCl | 0.5 | 0.027 | 0.706 | 0.116 | 0.235 |
| | 1 | 0.024 | 0.802 | 0.146 | 0.270 |
| | 1.5 | 0.020 | 0.820 | 0.140 | 0.307 |
| | 2 | 0.014 | 0.943 | 0.179 | 0.385 |
| | 2.5 | 0.008 | 1.039 | 0.183 | 0.455 |
| | 3 | 0.005 | 1.113 | 0.235 | 0.504 |
| | 3.5 | 0.003 | 0.970 | 0.248 | 0.528 |

Example 9

4) Examination of a Reducing Agent in the presence of an Acidifying Agent

30 μL mixed solution consisting of dithiothreitol, 2-mercaptoethylamine hydrochloride or 2-diethylaminoethanethiol hydrochloride as reducing agents dissolved in 1.0 N aqueous hydrochloric acid was added to 30 μL of an HBV antigen-negative sample (normal plasma) or three HBs antigen-positive samples (#990493, #990640, #990650) and then incubated at room temperature for 10 minutes, and 50 μL solution of the mixture was examined as a measurement sample by the method described in 1) (Table 11).

The reducing agent concentration used herein is the concentration thereof in the sample during treatment. Even when the reducing agent was added to the HBV antigen-negative sample, no change in its signal was recognized, but in one HBs antigen-positive sample (#990640), an increase of 30% or more was recognized with dithiothreitol at a concentration of 1 to 5 mM.

[Table 11]

TABLE 11

| | Reducing agent | | | | | | |
|---|---|---|---|---|---|---|---|
| | | HBV negative sample Serum from healthy person | HBV positive sample | | | | |
| | | | #990493 | | #990640 | | #990650 |
| | Concentration (mM) | | | % relative to control | | % relative to control | | % relative to control |
| Control Reducing agent added to 0.5N HCl | 0 | 0.012 | 0.446 | 100 | 0.073 | 100 | 0.159 | 100 |
| Dithiothreitol | 0.25 | 0.016 | 0.497 | 111 | 0.080 | 110 | 0.177 | 111 |
| | 0.5 | 0.014 | 0.487 | 109 | 0.083 | 114 | 0.184 | 116 |
| | 1 | 0.013 | 0.500 | 112 | 0.101 | 138 | 0.184 | 116 |
| | 2 | 0.012 | 0.453 | 102 | 0.124 | 170 | 0.174 | 109 |
| | 5 | 0.011 | 0.324 | 73 | 0.116 | 159 | 0.092 | 58 |
| | 10 | 0.007 | 0.082 | 18 | 0.040 | 55 | 0.033 | 21 |
| | 20 | 0.008 | 0.029 | 7 | 0.011 | 15 | 0.023 | 14 |
| 2-Mercaptoethyl amine Hydrochloride | 0.25 | 0.014 | 0.432 | 97 | 0.056 | 77 | 0.154 | 97 |
| | 0.5 | 0.009 | 0.429 | 96 | 0.064 | 88 | 0.144 | 91 |
| | 1 | 0.009 | 0.426 | 96 | 0.060 | 82 | 0.148 | 93 |
| | 2 | 0.008 | 0.411 | 92 | 0.069 | 95 | 0.129 | 81 |
| | 5 | 0.004 | 0.350 | 78 | 0.068 | 93 | 0.109 | 69 |
| | 10 | 0.001 | 0.278 | 62 | 0.075 | 103 | 0.074 | 47 |
| | 20 | 0.002 | 0.217 | 49 | 0.058 | 79 | 0.063 | 40 |
| | 50 | 0.000 | 0.140 | 31 | 0.037 | 51 | 0.033 | 21 |

TABLE 11-continued

| | | Reducing agent | | | | | | |
|---|---|---|---|---|---|---|---|---|
| | | HBV negative | HBV positive sample | | | | | |
| | | | #990493 | | #990640 | | #990650 | |
| | Concentration (mM) | sample Serum from healthy person | | % relative to control | | % relative to control | | % relative to control |
| 2-Diethylamino-ethanethiol Hydrochloride | 0.25 | 0.015 | 0.429 | 96 | 0.066 | 90 | 0.165 | 104 |
| | 0.5 | 0.012 | 0.429 | 96 | 0.067 | 92 | 0.156 | 98 |
| | 1 | 0.013 | 0.456 | 102 | 0.066 | 90 | 0.166 | 104 |
| | 2 | 0.008 | 0.436 | 98 | 0.083 | 114 | 0.151 | 95 |
| | 5 | 0.008 | 0.397 | 89 | 0.081 | 111 | 0.129 | 81 |
| | 10 | 0.004 | 0.298 | 67 | 0.085 | 116 | 0.090 | 57 |
| | 20 | 0.008 | 0.259 | 58 | 0.079 | 108 | 0.078 | 49 |
| | 50 | 0.006 | 0.145 | 33 | 0.065 | 89 | 0.049 | 31 |

Example 10

5) Concentration of an Alkalifying Agent

50 μL aqueous sodium hydroxide solution at various concentrations was added to 50 μL of an HBV antigen-negative sample or three anti-HBs antibody-containing HBV antigen-positive samples (#990493, #990640, #990650) and then incubated at room temperature for 10 minutes, and 50 μL solution of the mixture was examined as a measurement sample by the following measurement method.

The anti-HBs antigen monoclonal antibody 6G6 was diluted to a final concentration of 6 μg/ml with 10 mM phosphate buffer (pH 7.3) containing 0.15 M NaCl and then pipetted onto a 96-well microtiter plate (Nunc) in a volume of 100 μl per well. The plate was incubated at 4° C. overnight.

The plate was washed twice with 10 mM phosphate buffer, pH 7.3, containing 0.15 M NaCl, followed by adding 350 μl of 10 mM phosphate buffer, pH 7.1 containing 0.5% casein sodium and incubating the plate for 2 hours. After the blocking solution was removed, 100 μL reaction buffer containing a neutralizing agent, and the measurement samples obtained by each of the sample treatment method, were added to each well and reacted at room temperature for 2 hours under shaking, and washed 6 times with 350 μl of 10 mM phosphate buffer, pH 7.3, containing 0.05% Tween 20 (washing solution), followed by adding 100 μL of a biotin-labeled monoclonal antibody (HBs124). The mixture was reacted at room temperature for 30 minutes. Each well was then washed 6 times with the washing solution, then 100 μL of POD-labeled avidin D was added thereto, and the mixture was reacted at room temperature for 30 minutes. After each well was washed 6 times with the washing solution, 100 μl solution of a substrate (orthophenylene diamine, referred to hereinafter as OPD) was added thereto and incubated for 30 minutes, then 100 μl of 2 N sulfuric acid solution was added to each well which was then measured for its absorbance at a wavelength of 492 nm ($OD_{492}$) with its absorbance at a wavelength of 630 nm as the reference. The sodium hydroxide concentration shown in the table is the concentration during treatment after mixing the sample with the treatment agent.

The biotin-labeled monoclonal antibody HBs124 is a monoclonal antibody obtained by expressing and purifying a full-length HBs antigen (that is, an antigen consisting of the amino acid sequence in positions 1 to 226) as described in Example 1 and immunizing a mouse with the recombinant antigen. It was confirmed that the antibody HBs124 binds to the above recombinant HBs antigen. However, when synthetic peptides each consisting of 20 amino acids overlapping with each other by 10 amino acids were synthesized on the basis of the amino acid sequence in positions 1 to 226 in the HBs antigen and examined for their binding to the antibody HBs124 by the same method as in Example 3, the antibody HBs124 did not react with any of the synthetic peptides. Accordingly, it is estimated that the antibody HBs124 recognizes not a linear epitope of an amino acid sequence of HBs antigen, but a conformational epitope thereof.

HBs antigen activity could not be detected even by incubating the anti-HBs antibody-containing HBV-positive samples (#990493, #990640, #990650) in a solution not containing sodium hydroxide at room temperature for 10 minutes, but an increase in signal for HBs antigen was recognized in treatment with sodium hydroxide at a concentration of 0.25 to 1 N (Table 12).

[Table 12]

TABLE 12

| NaOH concentration (N) | HBV negative sample Serum from healthy person | HBV positive sample | | |
|---|---|---|---|---|
| | | #990493 | #990640 | #990950 |
| 0 | 0.006 | 0.005 | 0.006 | 0.006 |
| 0.05 | 0.006 | 0.010 | 0.004 | 0.002 |
| 0.1 | 0.010 | 0.014 | 0.010 | 0.008 |
| 0.25 | 0.006 | 0.034 | 0.006 | 0.012 |
| 0.5 | 0.008 | 0.058 | 0.006 | 0.030 |
| 0.75 | 0.004 | 0.070 | 0.006 | 0.039 |
| 1 | 0.010 | 0.044 | 0.018 | 0.042 |
| 1.5 | 0.008 | 0.012 | 0.014 | 0.029 |

Example 11

6) Various Surfactant Concentrations in the Presence of an Alkalifying Agent

30 μL of various surfactants dissolved in 1.0 N aqueous sodium hydroxide solution was added to 30 μL of an HBV antigen-negative sample or three HBs antigen-positive samples (#990493, #990640, #990650) and then incubated at room temperature for 10 minutes, and 50 μL solution of the mixture was examined as a measurement sample by the method described in 5) (Tables 13 to 17). The sodium hydroxide concentration and surfactant concentration shown in the tables are the concentrations during treatment after mixing the sample with the treatment agent.

As shown in Tables 13 to 17, the surfactant with which at least 1 of the 3 samples had shown higher reactivity than the judgment criteria of each sample was judged to be an effective surfactant. As a result, it was found that when various surfactants were added together with an alkalifying agent such as sodium hydroxide, there was a surfactant with which the immunoreactivity of the HBs antigen in the HBs antigen-positive sample was significantly increased. The surfactant judged to be effective includes an anionic surfactant such as sodium dodecyl sulfate or N-lauroyl sarcosine Na and an amphoteric or cationic surfactant having, in its molecule, a straight-chain alkyl group and a tertiary amine or quaternary ammonium salt.

Nonionic surfactants such as Triton X100, Tween 20 and Bridj 35 and a surfactant having a steroid skeleton, such as CHAPS, are also recognized to be effective.

An increase in measurable sensitivity was recognized by adding an anionic surfactant or an amphoteric or cationic surfactant having, in its molecule, a straight-chain alkyl group and a tertiary amine or a quaternary ammonium salt to an alkalifying agent. Such surfactant effective in the presence of an alkalifying agent in the treatment solution, when used in the treatment solution without the alkalifying agent, was not recognized to increase the measurable sensitivity. It was considered that by a combination of the alkalifying agent and the surfactant, the anti-HBs antibody acting as a factor inhibiting detection of HBs antigen is inactivated, and the epitope located inside a lipid bilayer of HBs antigen in a sample is exposed to the outside, thus significantly improving the reactivity thereof with 6G6.

[Table 13]

TABLE 13

| | | Anionic | | | |
|---|---|---|---|---|---|
| | Concentration | HBV negative sample Serum from healthy | HBV positive sample | | |
| | (%) | person | #990493 | #990640 | #990650 |
| No addition | 0 | 0.015 | 0.032 | 0.002 | 0.009 |
| Criteria for judging the effect of surfactant Surfactant added to 0.5N NaOH | | | 0.160 | 0.010 | 0.045 |
| Sodium Dodecyl Sulfate $CH_3(CH_2)_{11}OSO_3Na$ | 0.5 | 0.014 | 0.225 | 0.137 | 0.152 |
| | 1 | 0.015 | 0.340 | 0.241 | 0.195 |
| | 2 | 0.016 | 0.457 | 0.371 | 0.308 |
| | 5 | 0.015 | 0.967 | 0.430 | 0.472 |
| Lithium Dodecyl Sulfate $CH_3(CH_2)_{11}OSO_3Li$ | 0.5 | 0.009 | 0.239 | 0.168 | 0.132 |
| | 1 | 0.015 | 0.275 | 0.205 | 0.141 |
| | 2 | 0.007 | 0.468 | 0.416 | 0.272 |
| | 5 | 0.016 | 1.055 | 0.385 | 0.325 |
| N-Lauroylsarcosine sodium salt | 0.5 | 0.008 | 0.254 | 0.280 | 0.143 |
| | 1 | 0.004 | 0.391 | 0.354 | 0.274 |
| | 2 | 0.007 | 0.540 | 0.434 | 0.361 |
| | 5 | 0.007 | 0.769 | 0.618 | 0.482 |

[Table 14]

TABLE 14

| | | Cationic (TAC type) | | | |
|---|---|---|---|---|---|
| | Concentration | HBV negative sample Serum from | HBV positive sample | | |
| | (%) | healthy person | #990493 | #990640 | #990650 |
| No addition | 0 | 0.021 | 0.041 | 0.013 | 0.021 |
| Criteria for judging the effect of surfactant Surfactant added to 0.5N HCl | | | 0.205 | 0.065 | 0.105 |
| Octyltrimethyl-ammonium Chloride $[CH_3(CH_2)_7N(CH_3)_3]Cl$ | 0.5 | 0.020 | 0.163 | 0.120 | 0.209 |
| | 1 | 0.024 | 0.277 | 0.200 | 0.249 |
| | 2 | 0.021 | 0.409 | 0.147 | 0.167 |
| | 5 | 0.030 | 0.299 | 0.032 | 0.028 |

TABLE 14-continued

| | | Cationic (TAC type) | | |
|---|---|---|---|---|
| | Concentration (%) | HBV negative sample Serum from healthy person | HBV positive sample | |
| | | | #990493 | #990640 | #990650 |

| | Concentration (%) | Healthy | #990493 | #990640 | #990650 |
|---|---|---|---|---|---|
| Decyltrimethyl-ammonium Chloride $[CH_3(CH_2)_9N(CH_3)_3]Cl$ | 0.5 | 0.022 | 0.402 | 0.287 | 0.342 |
| | 1 | 0.022 | 0.418 | 0.151 | 0.131 |
| | 2 | 0.018 | 0.220 | 0.041 | 0.031 |
| | 5 | 0.025 | 0.067 | 0.023 | 0.019 |
| Dodecyltrimethyl-ammonium Chloride $[CH_3(CH_2)_{11}N(CH_3)_3]Cl$ | 0.5 | 0.021 | 0.513 | 0.351 | 0.341 |
| | 1 | 0.013 | 0.302 | 0.111 | 0.075 |
| | 2 | 0.019 | 0.069 | 0.028 | 0.041 |
| | 5 | 0.014 | 0.029 | 0.015 | 0.019 |
| Tetradecyltri-methylammonium Chloride $[CH_3(CH_2)_{13}N(CH_3)_3]Cl$ | 0.5 | 0.016 | 0.550 | 0.402 | 0.426 |
| | 1 | 0.013 | 0.359 | 0.184 | 0.100 |
| | 2 | 0.016 | 0.091 | 0.041 | 0.029 |
| | 5 | 0.015 | 0.061 | 0.017 | 0.024 |
| Hexadecyltri-methylammonium Chloride $[CH_3(CH_2)_{15}N(CH_3)_3]Cl$ | 0.5 | 0.020 | 0.566 | 0.326 | 0.466 |
| | 1 | 0.017 | 0.418 | 0.204 | 0.161 |
| | 2 | 0.021 | 0.179 | 0.041 | 0.036 |
| | 5 | 0.017 | 0.208 | 0.023 | 0.032 |
| Lauryl pyridinium Chloride $[C_5H_5NCH_2(CH_2)_{10}CH_3]Cl$ | 0.5 | 0.011 | 0.029 | 0.043 | 0.094 |
| | 1 | 0.010 | 0.022 | 0.049 | 0.062 |
| | 2 | 0.011 | 0.028 | 0.030 | 0.029 |
| | 5 | 0.049 | 0.043 | 0.039 | 0.036 |

[Table 15]

TABLE 15

| | | Cationic (TAB type) | | |
|---|---|---|---|---|
| | Concentration (%) | HBV negative sample Serum from healthy person | HBV positive sample | | |
| | | | #990493 | #990640 | #990650 |
| No addition | 0 | 0.007 | 0.031 | 0.005 | 0.011 |
| Criteria for judging the effect of surfactant Surfactant added to 0.5N NaOH | | | 0.155 | 0.025 | 0.055 |
| Octyltrimethylammonium Bromide $[CH_3(CH_2)_7N(CH_3)_3]Br$ | 0.5 | 0.008 | 0.134 | 0.094 | 0.180 |
| | 1 | 0.008 | 0.229 | 0.173 | 0.202 |
| | 2 | 0.009 | 0.403 | 0.152 | 0.135 |
| | 5 | 0.011 | 0.256 | 0.025 | 0.019 |
| Decyltrimethylammonium Bromide $[CH_3(CH_2)_9N(CH_3)_3]Br$ | 0.5 | 0.011 | 0.385 | 0.290 | 0.332 |
| | 1 | 0.015 | 0.379 | 0.121 | 0.068 |
| | 2 | 0.010 | 0.250 | 0.025 | 0.021 |
| | 5 | 0.014 | 0.037 | 0.012 | 0.012 |
| Dodecyltrimethyl-ammonium Bromide $[CH_3(CH_2)_{11}N(CH_3)_3]Br$ | 0.5 | 0.009 | 0.521 | 0.343 | 0.364 |
| | 1 | 0.007 | 0.346 | 0.118 | 0.063 |
| | 2 | 0.010 | 0.077 | 0.023 | 0.026 |
| | 5 | 0.009 | 0.041 | 0.008 | 0.015 |
| Tetradecyltrimethyl-ammonium Bromide $[CH_3(CH_2)_{13}N(CH_3)_3]Br$ | 0.5 | 0.008 | 0.577 | 0.381 | 0.438 |
| | 1 | 0.008 | 0.419 | 0.190 | 0.099 |
| | 2 | 0.009 | 0.109 | 0.031 | 0.028 |
| | 5 | 0.010 | 0.126 | 0.013 | 0.017 |
| Hexadecyltrimethyl-ammonium Bromide $[CH_3(CH_2)_{15}N(CH_3)_3]Br$ | 0.5 | 0.011 | 0.611 | 0.335 | 0.440 |
| | 1 | 0.011 | 0.437 | 0.234 | 0.183 |
| | 2 | 0.011 | 0.253 | 0.079 | 0.061 |
| | 5 | 0.011 | 0.067 | 0.013 | 0.019 |

[Table 16]

TABLE 16

| | | Amphoteric | | |
| --- | --- | --- | --- | --- |
| | | HBV negative sample Serum from healthy | HBV positive sample | |
| | Concentration (%) | person | #990493 | #990640 | #990650 |
| No addition | 0 | 0.008 | 0.027 | 0.004 | 0.010 |
| Criteria for judging the effect of surfactant Surfactant added to 0.5N NaOH | | | 0.135 | 0.020 | 0.050 |
| 3-[3-(Cholamidopropyl) dimethyl-ammonio]-1-propanesulfonate | 0.5 | 0.006 | 0.396 | 0.183 | 0.200 |
| | 1 | 0.007 | 0.496 | 0.201 | 0.267 |
| | 2 | 0.008 | 0.660 | 0.204 | 0.359 |
| | 5 | 0.007 | 0.709 | 0.139 | 0.290 |
| N-Dodecyl-N,N-dimethyl-3-ammonio-1-propanesulfonate $CH_3(CH_2)_{11}N(CH_3)_2[(CH_2)_3SO_3]$ | 0.5 | 0.010 | 0.251 | 0.247 | 0.122 |
| | 1 | 0.008 | 0.292 | 0.288 | 0.140 |
| | 2 | 0.012 | 0.330 | 0.188 | 0.147 |
| | 5 | 0.006 | 0.268 | 0.105 | 0.119 |
| N-Tetradecyl-N,N-dimethyl-3-ammonio-1-propanesulfonate $CH_3(CH_2)_{13}N(CH_3)_2[(CH_2)_3SO_3]$ | 0.5 | 0.008 | 0.339 | 0.308 | 0.230 |
| | 1 | 0.007 | 0.419 | 0.347 | 0.187 |
| | 2 | 0.009 | 0.522 | 0.357 | 0.185 |
| | 5 | 0.008 | 1.037 | 0.451 | 0.218 |
| N-Hexadecyl-N,N-dimethyl-3-ammonio-1-propanesulfonate $CH_3(CH_2)_{15}N(CH_3)_2[(CH_2)_3SO_3]$ | 0.5 | 0.010 | 0.370 | 0.254 | 0.341 |
| | 1 | 0.008 | 0.527 | 0.324 | 0.278 |
| | 2 | 0.010 | 0.834 | 0.551 | 0.336 |
| | 5 | 0.005 | 1.110 | 0.451 | 0.257 |

[Table 17]

TABLE 17

| | | Nonionic | | |
| --- | --- | --- | --- | --- |
| | Concentration (%) | HBV negative sample Serum from healthy person | HBV positive sample | |
| | | | #990493 | #990640 | #990650 |
| No addition | 0 | 0.022 | 0.044 | 0.013 | 0.025 |
| Criteria for judging the effect of surfactant Surfactant added to 0.5N NaOH | | | 0.220 | 0.065 | 0.125 |
| Triton X-100 | 0.5 | 0.021 | 0.305 | 0.174 | 0.108 |
| | 1 | 0.021 | 0.344 | 0.168 | 0.121 |
| | 2 | 0.019 | 0.367 | 0.185 | 0.166 |
| | 5 | 0.018 | 0.299 | 0.188 | 0.164 |
| Triton X-114 | 0.5 | 0.023 | 0.293 | 0.128 | 0.111 |
| | 1 | 0.023 | 0.356 | 0.172 | 0.190 |
| | 2 | 0.020 | 0.404 | 0.173 | 0.250 |
| | 5 | 0.024 | 0.528 | 0.271 | 0.287 |
| Tween 20 | 0.5 | 0.020 | 0.094 | 0.033 | 0.063 |
| | 1 | 0.017 | 0.215 | 0.070 | 0.093 |
| | 2 | 0.021 | 0.345 | 0.187 | 0.250 |
| | 5 | 0.017 | 0.274 | 0.117 | 0.173 |
| Tween 80 | 0.5 | 0.017 | 0.104 | 0.038 | 0.081 |
| | 1 | 0.016 | 0.266 | 0.116 | 0.169 |
| | 2 | 0.020 | 0.379 | 0.212 | 0.215 |
| | 5 | 0.015 | 0.271 | 0.163 | 0.141 |

TABLE 17-continued

| | | Nonionic | | |
| --- | --- | --- | --- | --- |
| | Concentration (%) | HBV negative sample Serum from healthy person | HBV positive sample | |
| | | | #990493 | #990640 | #990650 |
| Bridj 35 | 0.5 | 0.021 | 0.317 | 0.190 | 0.143 |
| | 1 | 0.016 | 0.260 | 0.193 | 0.150 |
| | 2 | 0.020 | 0.301 | 0.255 | 0.151 |
| | 5 | 0.017 | 0.365 | 0.278 | 0.207 |

Example 12

7) Protein Denaturant in the Presence of an Alkalifying Agent

30 µL of a protein denaturant (urea or guanidine hydrochloride) dissolved in 1.0 N aqueous sodium hydroxide solution was added to 30 µL of an HBs antigen-negative sample or three HBs antigen-positive samples (#990493, #990640, #990650) and then incubated at room temperature for 10 minutes, and 50 µL solution of the mixture was examined as a measurement sample by the method described in 5). The immunoreactivity of each HBs antigen-positive sample is shown in Table 18. The sodium hydroxide concentration and protein denaturant concentration shown in Table 18 are the concentrations during treatment after mixing the sample with the treatment agent.

The three HBs antigen-positive samples showed higher immunoreactivity with the protein denaturant in the presence of the alkalifying agent than with the alkalifying agent only; that is, the immunoreactivity was increased at least about 8-fold with urea or at least about 4.5-fold with guanidine hydrochloride. In the case of treatment with the alkalifying agent only, serum protein or the like may be denatured at the time of neutralization to cause precipitation or to become turbid in some cases so that the pipetting procedure is hindered and precipitates are often a major cause of giving a false-positive result. There may also occur a reduction in sensitivity attributable to incorporation of the objective antigen into such precipitates. It was revealed that formation of such precipitates can be significantly reduced by adding urea or guanidine hydrochloride at a concentration of 1 M or more at the time of treatment, and this effect is made particularly higher by adding urea at a concentration of 2 to 4 M and guanidine hydrochloride at a concentration of 2 to 3 M at the time of treatment.

[Table 18]

TABLE 18

|  | Concentration (M) | HBV negative sample Serum from healthy person | HBV positive sample | | |
|---|---|---|---|---|---|
|  |  |  | #990493 | #990640 | #990650 |
| No addition Protein denaturant added to 0.5N NaOH | 0 | 0.015 | 0.032 | 0.002 | 0.009 |
| Urea | 1 | 0.006 | 0.072 | 0.017 | 0.074 |
|  | 2 | 0.005 | 0.168 | 0.048 | 0.186 |
|  | 3 | 0.007 | 0.263 | 0.133 | 0.305 |
|  | 4 | 0.004 | 0.267 | 0.179 | 0.334 |

TABLE 18-continued

|  | Concentration (M) | HBV negative sample Serum from healthy person | HBV positive sample | | |
|---|---|---|---|---|---|
|  |  |  | #990493 | #990640 | #990650 |
| Guanidine-HCl | 0.5 | 0.008 | 0.037 | 0.017 | 0.070 |
|  | 1 | 0.006 | 0.052 | 0.025 | 0.096 |
|  | 2 | 0.006 | 0.121 | 0.065 | 0.147 |
|  | 3 | 0.015 | 0.152 | 0.111 | 0.144 |

Example 13

8) Examination of a Reducing Agent in the Presence of an Alkalifying Agent

30 µL of a dithiothreitol, 2-mercaptoethylamine hydrochloride, diethylaminoethanethiol hydrochloride, 2-mercaptoethanol or tri(2-carboxyethyl)phosphine hydrochloride as reducing agents dissolved in 1.0 N sodium hydroxide was added to 30 µL of an HBV antigen-negative samples or three HBs antigen-positive samples (#990493, #990640, #990650) and then incubated at room temperature for 10 minutes, and 50 µL solution of the mixture was examined as a measurement sample by the method described in 5) (Table 19).

The reducing agent concentration used herein is the concentration thereof in the sample during treatment. The HBV antigen-negative sample hardly showed a change in signal even by adding the reducing agent, but all the three HBs antigen-positive samples showed an about 2- to 3-fold increase in signal with 2-mercaptoethylamine hydrochloride, diethylaminoethanethiol hydrochloride and 2-mercaptoethanol at a concentration of 20 mM respectively. Tri(2-carboxyethyl)phosphine hydrochloride is more effective by which a 1.5-fold increase in signal was recognized at a concentration of 2 mM and a 15-fold or more increase in signal was recognized at a concentration of 10 mM.

[Table 19]

TABLE 19

| Reducing agent | Concentration (mM) | HBV negative sample Serum from healthy person | HBV positive sample | | |
|---|---|---|---|---|---|
|  |  |  | #990493 | #990640 | #990650 |
| No addition Reducing agent added to 0.5N NaOH | 0 | 0.017 | 0.053 | 0.020 | 0.032 |
| Dithiothreitol | 2 | 0.017 | 0.063 | 0.023 | 0.039 |
|  | 5 | 0.016 | 0.058 | 0.019 | 0.041 |
|  | 10 | 0.019 | 0.067 | 0.024 | 0.051 |
|  | 20 | 0.019 | 0.089 | 0.025 | 0.050 |
| 2-Mercaptoethylamine Hydrochloride | 2 | 0.027 | 0.074 | 0.028 | 0.043 |
|  | 5 | 0.016 | 0.066 | 0.023 | 0.036 |
|  | 10 | 0.017 | 0.086 | 0.038 | 0.058 |
|  | 20 | 0.016 | 0.154 | 0.078 | 0.114 |
| 2-Diethylamino-ethanethiol Hydrochloride | 2 | 0.027 | 0.066 | 0.029 | 0.035 |
|  | 5 | 0.023 | 0.052 | 0.031 | 0.043 |
|  | 10 | 0.029 | 0.065 | 0.067 | 0.075 |
|  | 20 | 0.022 | 0.094 | 0.307 | 0.197 |

TABLE 19-continued

| | | Reducing agent | | | |
|---|---|---|---|---|---|
| | Concentration (mM) | HBV negative sample Serum from healthy person | HBV positive sample | | |
| | | | #990493 | #990640 | #990650 |
| 2-Mercaptoethanol | 2 | 0.027 | 0.082 | 0.033 | 0.047 |
| | 5 | 0.023 | 0.084 | 0.030 | 0.046 |
| | 10 | 0.025 | 0.109 | 0.041 | 0.058 |
| | 20 | 0.024 | 0.160 | 0.064 | 0.104 |
| Tri(2-carboxyethyl) phosphine Hydrochloride | 2 | 0.031 | 0.085 | 0.036 | 0.070 |
| | 5 | 0.028 | 0.141 | 0.042 | 0.104 |
| | 10 | 0.066 | 0.861 | 0.437 | 0.689 |
| | 20 | 0.131 | 0.495 | 0.534 | 0.479 |

The invention claimed is:

1. A method of detecting hepatitis B virus or hepatitis B virus s antigen, the method comprising contacting a sample with an antibody, wherein the antibody recognizes an epitope located on a peptide consisting of the amino acids at the positions 6 to 25 of the amino acid sequence set forth in SEQ ID NO: 1 corresponding to positions 31 to 50 in a hepatitis B virus s antigen.

2. The detection method according to claim 1, said method further comprising adding to the sample a denaturant.

3. The detection method according to claim 2, wherein the denaturant is a surfactant.

4. The detection method according to claim 2, wherein the denaturant is a surfactant and said method further comprises adding to the sample an acidifying agent, and wherein the addition of the surfactant and the acidifying agent results in dissociation of hepatitis B virus s antigen and inactivation of a patient's antibody binding to hepatitis B virus s antigen.

5. The detection method according to claim 2, wherein the denaturant is a surfactant and said method further comprises adding to the sample an alkalifying agent, and wherein the addition of the surfactant and the alkalifying agent results in dissociation of hepatitis B virus s antigen and inactivation of a patient's antibody binding to hepatitis B virus s antigen.

6. The detection method according to claim 2, wherein the denaturant is a surfactant and/or a reducing agent and said method further comprises adding to the sample an alkalifying agent, and wherein the addition of the surfactant and/or the reducing agent and the alkalifying agent results in dissociation of hepatitis B virus s antigen and inactivation of a patient's antibody binding to hepatitis s B virus s antigen.

7. The detection method according to claim 1, said method further comprising contacting the sample with an antibody that recognizes a hepatitis B virus antigen other than a hepatitis B virus s antigen.

* * * * *